(12) United States Patent
Lecuivre

(10) Patent No.: US 10,472,750 B2
(45) Date of Patent: Nov. 12, 2019

(54) PROSTHESIS COMPRISING A THREE-DIMENSIONAL AND OPENWORKED KNIT

(71) Applicant: Sofradim Production, Trévoux (FR)

(72) Inventor: Julie Lecuivre, Rhone (FR)

(73) Assignee: Sofradim Production, Trevoux (FR)

( * ) Notice: Subject to any disclaimer, the term of this patent is extended or adjusted under 35 U.S.C. 154(b) by 199 days.

(21) Appl. No.: 15/419,860

(22) Filed: Jan. 30, 2017

(65) Prior Publication Data

US 2017/0135797 A1 May 18, 2017

Related U.S. Application Data

(63) Continuation of application No. 14/003,529, filed as application No. PCT/EP2012/054709 on Mar. 16, 2012, now Pat. No. 9,554,887.

(30) Foreign Application Priority Data

Mar. 16, 2011 (FR) ...................................... 11 52167

(51) Int. Cl.
*D04B 21/12* (2006.01)
*D04B 21/10* (2006.01)
*A61L 27/16* (2006.01)
*A61L 27/34* (2006.01)
*A61F 2/00* (2006.01)

(52) U.S. Cl.
CPC ............ *D04B 21/12* (2013.01); *A61F 2/0063* (2013.01); *A61L 27/16* (2013.01); *A61L 27/34* (2013.01); *D04B 21/10* (2013.01); *A61F 2002/009* (2013.01); *A61F 2002/0068* (2013.01); *A61F 2210/0076* (2013.01); *A61F 2230/0008* (2013.01); *A61F 2240/001* (2013.01); *A61F 2250/0031* (2013.01);
(Continued)

(58) Field of Classification Search
CPC ........ D04B 21/12; D04B 21/06; D04B 21/08; D04B 21/10; D04B 21/20
See application file for complete search history.

(56) References Cited

U.S. PATENT DOCUMENTS 1,187,158 A 6/1916 McGinley
3,054,406 A 9/1962 Usher
(Continued)

FOREIGN PATENT DOCUMENTS

CA 1317836 C 5/1993
CN 201879864 U 6/2011
(Continued)

OTHER PUBLICATIONS

International Search Report for PCT/EP12/54709 date of completion is Jun. 22, 2012 (3 pages).
(Continued)

*Primary Examiner* — Danny Worrell

(57) ABSTRACT

The present invention relates to a prosthesis (100) comprising an openworked three-dimensional knit (101) comprising a front face and a rear face, each face being formed with one or more laps of yarns defining pores on said face, the front face being bound to the rear face by connecting yarns defining a spacer, characterized in that the connecting yarns are distributed so that they define an entanglement of yarns crossing each other at the spacer, without obstructing the pores of the front and rear faces.

24 Claims, 6 Drawing Sheets

Figure 1:
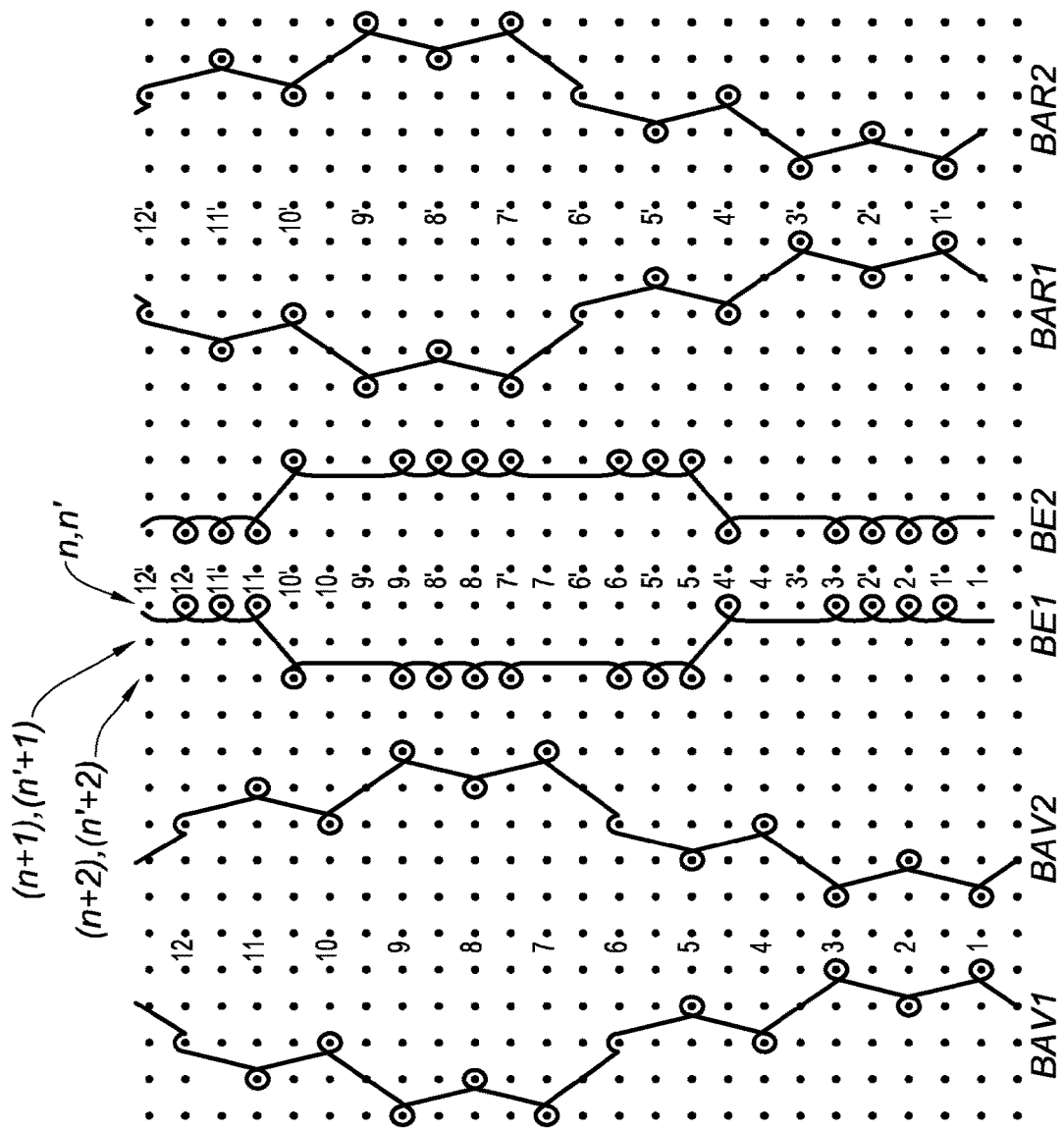

(52) U.S. Cl.
CPC .............. *A61F 2250/0051* (2013.01); *D10B 2403/0213* (2013.01); *D10B 2509/08* (2013.01)

(56) References Cited

U.S. PATENT DOCUMENTS

| | | |
|---|---|---|
| 3,118,294 A | 1/1964 | Van Laethem |
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A | 11/1994 | de la Torre |
| 5,370,650 A | 12/1994 | Tovey et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Voumakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |

(56) References Cited

U.S. PATENT DOCUMENTS

| | | |
|---|---|---|
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Rinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakamam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B1 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |

(56) References Cited

U.S. PATENT DOCUMENTS

| | | | |
|---|---|---|---|
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,933,290 B2 | 1/2015 | Lefranc et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,186,235 B2 | 11/2015 | Ory et al. |
| 9,211,175 B2 | 12/2015 | Stopek et al. |
| 9,216,075 B2 | 12/2015 | Bailly et al. |
| 9,242,026 B2 | 1/2016 | Bayon et al. |
| 9,554,887 B2 | 1/2017 | Lecuivre |
| 2002/0034901 A1 | 3/2002 | Fujita et al. |
| 2002/0087174 A1 | 7/2002 | Capello |
| 2002/0095218 A1 | 7/2002 | Carr et al. |
| 2003/0086975 A1 | 5/2003 | Ringeisen |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0228408 A1 | 10/2005 | Fricke et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036907 A1 | 2/2009 | Bayon et al. |
| 2009/0036996 A1 | 2/2009 | Roeber |
| 2009/0068250 A1 | 3/2009 | Gravagna et al. |
| 2009/0105526 A1 | 4/2009 | Piroli Torelli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li |
| 2009/0318752 A1 | 12/2009 | Evans et al. |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |

(56) References Cited

U.S. PATENT DOCUMENTS

| | | |
|---|---|---|
| 2012/0150204 A1 | 6/2012 | Mortarino et al. |
| 2012/0165937 A1 | 6/2012 | Montanari et al. |
| 2012/0179175 A1 | 7/2012 | Hammell |
| 2012/0179176 A1 | 7/2012 | Wilson et al. |
| 2012/0197415 A1 | 8/2012 | Montanari et al. |
| 2014/0044861 A1 | 2/2014 | Boey et al. |
| 2014/0364684 A1 | 12/2014 | Lecuivre |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1158082 A2 | 11/2001 |
| EP | 1216717 A1 | 6/2002 |
| EP | 1216718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2002-518129 A | 6/2002 |
| JP | 2003517318 A | 5/2003 |
| JP | 2008538300 A | 10/2008 |
| JP | 2009503281 A | 1/2009 |
| JP | 2011078767 A | 4/2011 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9310731 A1 | 6/1993 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 2001081667 A1 | 11/2001 |
| WO | 2002/007648 | 1/2002 |
| WO | 0217853 A2 | 3/2002 |
| WO | 0250352 A1 | 6/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2007048099 A2 | 4/2007 |
| WO | 2009031035 A2 | 3/2009 |
| WO | 2009071998 A2 | 6/2009 |
| WO | 2010043978 A2 | 4/2010 |
| WO | 2010052585 A2 | 5/2010 |
| WO | 2011007062 A1 | 1/2011 |
| WO | 2011026987 A1 | 3/2011 |
| WO | 2011038740 A1 | 4/2011 |

OTHER PUBLICATIONS

Australian Office Action dated Apr. 6, 2016 in corresponding Australian Patent Application No. 2012228190, 3 pages.

(56) References Cited

OTHER PUBLICATIONS

Ellouali, M. et al., "Antitumor Activity of Low Molecular Weight Fucans Extracted from Brown Seaweed Ascophyllum nodosum," Anticancer Res., Nov.-Dec. 1993, pp. 2011-2020, 12 (6A).

Malette, W. G. et al., "Chitosan, a New Hemostatic," Ann Th. Surg., Jul. 1983, pp. 55-58, 36.

Langenbech, M. R. et al., "Comparison of biomaterials in the early postoperative period," Surg Endosc., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4). cited byapplicant.

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2),published online Nov. 2009.

Junge, K. et al., "Functional and Morphologic Properties of a Modified Mesh for Inguinal Hernia Repair," World J. Surg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004,pp. 211-220,18(2).

Blondin, C. et al., "Inhibition of Complement Activation by Natural Sulfated Polysaccharides (Fucans) from Brown Seaweed," Molecular Immuol., Mar. 1994, pp. 247-253, 31(4).

Zvyagintseva, T. et al., "Inhibition of complement activation by water-soluble polysaccharides of some far-eastern brown seaweeds," Comparative Biochem and Physiol, Jul. 2000, pp. 209-215,126(3).

Rosen, M. et al., "Laparoscopic component separation in the single-stage treatment of infected abdominal wall prosthetic removal," Hernia, 2007, pp. 435-440, 11, published online Jul. 2007.

Amid, P., "Lichtenstein tension-free hernioplasty: Its inception, evolution, and principles," Hernia, 2004; pp. 1-7, 8, published online Sep. 2003.

Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).

O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).

Muzzarelli, R. et al., "Reconstruction of parodontal tissue with chitosan," Biomaterials, Nov. 1989, pp. 598-604, 10.

Haroun-Bouhedja, F. et al., "Relationship between sulfate groups and biological activities of fucans," Thrombosis Res., Dec. 2000, pp. 453-459, 100(5).

Blondin, C. et al., "Relationships between chemical characteristics and anticomplementary activity of fucans," Biomaterials, Mar. 1996, pp. 597-603, 17(6).

Strand, S. et al., "Screening of Chitosans and Conditions for Bacterial Flocculation," Biomacromolecules, Mar. 2001, 126-133, 2.

Kanabar, V. et al., "Some structural determinants of the antiproliferative effect of heparin-like molecules on human airway smooth muscle," Br. J. Pharmacol., Oct. 2005, pp. 370-777, 146(3).

Hirano, S. et al., "The blood biocompatibility of chitosan and N-acylchitosans," J. Biomed. Mater. Res., Apr. 1985, 413-417, 19.

Rao, B. et al., "Use of chitosan as a biomaterial: Studies on its safety and hemostatic potential," J. Biomed. Mater. Res., Jan. 1997, pp. 21-28, 34.

Prokop, A. et al., "Water Soluble Polymers for Immunoisolation I: Complex Coacevation and Cytotoxicity," Advances in Polymer Science, Jul. 1998, pp. 1-51, 136.

Collins, R. et al., "Use of collagen film as a dural substitute: Preliminary animal studies," Journal of Biomedical Materials Research, Feb. 1991, pp. 267-276, vol. 25.

Preliminary Search Report from French Patent Office dated Dec. 20, 2006, 3 pages.

JP Office Action dated Jan. 29, 2016 in corresponding JP Patent Application No. 2013-558462, together with English language translation.

Notice of Allowance issued by the Japanese Patent Office in corresponding Japanese Patent Application No. 2013-558462 dated Oct. 4, 2016 with English summary, 5 pages.

Canadian Office Action dated Nov. 6, 2017 in corresponding Canadian Patent Application No. 2,829,710, 3 pages.

PROSTHESIS COMPRISING A THREE-DIMENSIONAL AND OPENWORKED KNIT

CROSS-REFERENCE TO RELATED APPLICATIONS

This application is a continuation of U.S. patent application Ser. No. 14/003,529 filed Sep. 6, 2013, which is a National Stage Application of PCT/EP12/54709 under 35USC § 371 (a), which claims benefit of and priority to French Patent Application Serial No. 11/52167 filed Mar. 16, 2011, the disclosures of each of the above-identified applications are hereby incorporated by reference in their entirety.

The invention relates to a prosthesis comprising an openworked three-dimensional knit, for example useful as a wall reinforcement in parietal and/or visceral surgery.

By three-dimensional knit, in the sense of the present application, is meant a knit having a front face and a rear face, each face being formed with one or more laps of yarns, the front face being bound to the rear face through connecting yarns defining a spacer. The presence of the spacer thereby provides some thickness to the knit: such three-dimensional knits may be obtained with a knitting machine of the warp type or two-bed Rachel type.

By openworked knit, in the sense of the present application, is meant the feature according to which the knit has pores, or further open voids, cells, holes or orifices, either regularly distributed or not, promoting cell colonization. The pores may appear in any kinds of shapes such as for example, spheres, channels, hexagonal shapes.

The spacer as defined above may be formed either with certain yarns of the lap(s) of one of the two faces, which regularly leave their original face for producing a stitch on the other face, and then return to their original lap, or on the contrary with one or more laps of yarns which are dedicated to the spacer and which run to and fro from one face to the other of the knit without being significantly involved in producing each face.

Openworked three-dimensional knits with a spacer connecting the front face to the rear face of the knit are already known. Thus document WO99/05990 describes openworked three-dimensional knits, the spacer of which is produced by one or more laps of connecting yarns dedicated to the formation of said spacer. As indicated in this document, the connecting yarns extend perpendicularly from one face towards the other and form transverse channels parallel with each other.

When they are subject to a compressive force, tending to press the front face of the knit onto its rear face, or tensile force, the knits as described in WO99/05990 may see the spacer «be laid down» or "fall" under this stress, so as to reach a position almost parallel to each of both faces: such a phenomenon causes sliding of the front face relatively to the rear face, this may cause a shift of the pores of the front face relatively to the pores of the rear face. The knit undergoes a«flattening» phenomenon and the walls of the pores of one face may move and obstruct the pores of the other face. The knit then loses its capability of promoting cell recolonization. Moreover, it is no longer possible to see in transparence through the knit, which may be a difficulty for the surgeon upon setting into place a reinforcement prosthesis for example made from such a knit.

Thus, it would be desirable to have a prosthesis comprising an openworked three-dimensional knit, having a spacer capable of withstanding compression and tension, in particular with view to avoiding deformation, and in particular with a view to avoiding collapse, of the knit when the latter is subject to such stresses. It would also be desirable to provide such an improved prosthesis without having to add too much of material forming the knit, in a view to limit foreign material intended to be implanted in the body of a patient.

The object of the present invention is to provide a prosthesis comprising an openworked three-dimensional knit retaining its three-dimensional structure even when it is subject to compressive forces, for example from one face onto the other, or to tensile forces.

The present invention relates to a prosthesis comprising at least one openworked three-dimensional knit comprising two opposite faces, for example a front face and a rear face, each face being formed with one or more laps of yarns defining pores on said face, one face being bound to the opposite face by connecting yarns defining a spacer, characterized in that the connecting yarns are distributed so that they define an entanglement of yarns which cross each other at the spacer, without obstructing the pores of the two opposite faces.

Thus, unlike the knits of the prior art, the connecting yarns of the knit of the prosthesis according to the invention do not form parallel channels with each other and perpendicular to the faces of the knit. On the contrary, in the knit of the prosthesis according to the invention, the yarns of the spacer run from one face to the other of the knit obliquely and not in parallel, i.e. these yarns cross each other, giving the spacer an «X profile» («X-stitch») or «crossed profile». In the knit of the prosthesis according to the invention, at least part of the connecting yarns forming the spacer cross each other, giving the knit significant stability of its three-dimensional structure, even when the knit is subject to compressive forces, tending to press its front face onto its rear face. Thus, in the knit of the prosthesis according to the invention, the spacer does not tend to place itself in a position parallel to both faces of the knit when the knit is subject to compressive forces, and the front face does not slide relatively to the rear face. With the knit of the prosthesis according to the invention, the front face remains facing the rear face, without any shift, when the knit is subject to compressive forces. Thus, the pores of the front face and the pores of the rear face, which for example are facing each other when the knit is at rest, remain in the same relative position even when the knit is subject to compressive forces. The transparence of the knit of the prosthesis according to the invention may thereby be maintained in both situations.

Further, the knit of the prosthesis according to the invention retains a good capability for cell recolonization, even under compression or under tension, the pores of the front face not being obstructed by yarns forming the walls of the pores of the rear face. The knit of the prosthesis according to the invention retains its three-dimensional structure even under compression or under tension.

Resistance to suture of the knit of the prosthesis according to the invention is also excellent.

In one embodiment, one face being formed with r rows and n columns of stitches, located facing r' rows and n' columns of stitches forming the opposite face, with at least one portion of the connecting yarns, at either regular row number intervals or not, connects a column $n_i$ of one of the two faces to the column ($n_i'$+x), wherein x ranges from 2 to 5, of the opposite face, and, at either regular row number intervals or not, connects a column $n_j$ of one of the two faces to the column ($n_j'$−x') of the opposite face, wherein x' ranges from 2 to 5.

In one embodiment, the row number intervals are regular. An optimum entanglement of connecting yarns crossing each other is thereby obtained.

In one embodiment, x=x', for example, x=x'=2. This means that either regularly or not, each connecting yarn connects a column $n_i$ of one of the two faces, not to the column $n_i'$ located facing the column $n_i$ on the opposite face, but to the column ($n_i'+2$) of the opposite face, i.e. to a column of the opposite face shifted by two columns in a first direction with respect to the column $n_i'$ of the opposite face. Thus, the connecting yarn is not perpendicular to the faces of the knit but is oblique relatively to these faces. Further, either regularly or not, this yarn also connects a column $n_j$, which may for example be the column ($n_i'+2$) above or not, of one of the two faces to another column ($n_i'-2$) of the opposite face, i.e. shifted by two columns in the direction opposite to the first direction. Thus, on the whole of the knit of the prosthesis according to the invention, connecting yarns regularly cross each other at the spacer. The three-dimensional stability of the spacer, and therefore of the knit, is reinforced. In another embodiment, x=x'=3. In such a case, each connecting yarn runs back on the opposite face to a column shifted by three columns relatively to its original column of the starting face, in one direction and then in the other. In still another embodiment, x=x'=4. In such a case, each connecting yarn runs back onto the opposite face, to a column shifted by four columns relatively to its original column of the starting face, in one direction and then in the other.

In another embodiment, x is different from x'. For example, the connecting yarn is shifted by 2 columns when it connects one of the two faces to the opposite face in a lateral direction of the knit and is then shifted by 3 columns when it again connects one of the two faces to the opposite face, in the opposite lateral direction.

In one embodiment of the invention, the connecting yarns are yarns from at least one lap among the laps forming both opposite faces. In such an embodiment, the knit of the prosthesis according to the invention preferably does not comprise any additional yarn laps for producing the spacer. Thus, this is, for example, one or more of the lap(s) making up the front face which include(s) at regular intervals, stitches caught with the stitches of one or more of the lap(s) of the rear face, in order to ensure the connection between both faces. With such embodiments it is possible to limit the amount of yarns present in the knit of the prosthesis according to the invention, while obtaining a spacer having a good resistance to compressive forces. Thus, the pores of the front face and the pores of the rear face remain in the same relative position even when the knit is subject to compressive forces. The transparency of the knit is maintained even when the knit is subject to compressive forces. In addition, embodiments where the connecting yarns are yarns from at least one lap among the laps forming both opposite faces allow obtaining an optimal combination between on one hand the three-dimensional porous structure of the knit, for a good cell colonization, and on the other hand the thickness of the knit, which must not be too great in order to facilitate the introduction of the knit in a trocar in case the prosthesis is implanted via a trocar.

In another embodiment, the connecting yarns are yarns from one or more laps dedicated to the formation of the spacer. With such embodiments it is possible to use different yarns for forming the spacer with respect to the yarns used for forming the front face and/or the rear face, and to thus impart different properties, for example resorption properties to the spacer.

Both opposite faces, for example the front face and the rear face and the spacer of the knit of the prosthesis according to the invention may be made in any biocompatible, monofilament and/or multi-filament yarn either bioresorbable or not, customarily used in the making of prosthetic knits.

In embodiments, the connecting yarns define in addition a set of parallel or oblique yarns not crossing each other and not obstructing the pores of the two opposite faces. This set of parallel or oblique yarns not crossing each other and not obstructing the pores of the two opposite faces form additional connections between the front and the rear face which, in particular when such connecting yarns are yarns from one lap from the laps forming both opposite faces, bring additional resistance to compressive force to the knitted structure. In particular, the stability of the three-dimensional structure of the knit is increased, and the knit thus obtained shows a three-dimensional structure particularly capable of resisting to flattening and collapsing when a compressive force is applied onto the knit.

The present invention further relates to a prosthesis comprising at least one openworked three-dimensional knit comprising two opposite faces, for example a front face and a rear face, each face being formed with one or more laps of yarns defining pores on said face, one face being bound to the opposite face by connecting yarns defining a spacer, the connecting yarns being distributed so that they define an entanglement of yarns crossing each other at the spacer, without obstructing the pores of the two opposite faces, said knit being obtainable by knitting on a knitting machine of the warp or Rachel type comprising two opposite beds, each respectively with m and m' needles, the needles m of one bed facing the needles m' of the opposite bed, the connecting yarns being distributed over at least one guide bar BE1, said bar BE1 having at least one lateral movement in one direction from one needle $m_i$ of one of the two beds to a needle ($m_i'+x$) of the opposite bed, wherein x ranges from 2 to 5, and a lateral movement in the opposite direction from one needle $m_j$ of one of the two beds to a needle ($m_j'-x'$) of the opposite bed, wherein x' ranges from 2 to 5.

Thus, during the knitting of the knit, a connecting yarn leaves a needle $m_i$ of one face in order to connect either regularly or not, not the needle $m_i'$ of the opposite face, but a needle shifted by 2, 3, 4 or 5 needles in a first direction with respect to the needle $m_i'$. Also, either regularly or not, the connecting yarn connects a needle $m_j$ of one face to a needle of the opposite face, shifted by 2, 3, 4 or 5 needles in the direction opposite to the first direction relatively to the needle $m_j'$.

In an embodiment of the prosthesis according to the invention, the knit is formed by knitting threaded yarns, one full stitch, one empty stitch, on four guide bars BAV, BE1, BAR1 and BAR2, the bars BAV and BE1 forming two laps of yarns producing the front face, the bars BAR1 and BAR2 forming two laps of yarns producing the rear face and the bar BE1 forming the spacer. In such embodiments, it is the yarns of the front face which achieve the connection between both faces and which therefore form the spacer. Thus, the bar BE1 is involved in both the formation of a lap of the front face and in the formation of the spacer.

In an embodiment of the prosthesis according to the invention, the knit is formed by knitting threaded yarns, one full stitch, one empty stitch, on four guide bars BAV, BE1, BAR1 and BAR2, the bars BAV and BE1 forming two laps of yarns producing the front face, the bars BAR1 and BAR2 forming two laps of yarns producing the rear face and the bar BE1 forming the spacer, said laps being knitted according to the scheme below according to the ISO 11676 standard:

BAV:4.3.2.2/1.0.1.1/1.2.1.1/1.0.1.1/1.2.1.1/1.0.1.1/ 1.2.3.3/4.5.4.4/4.3.4.4/4.5.4.4/4.3.4.4/4.5.4.4//

BE1:1.2.3.3/4.5.1.2/4.3.4.4/4.5.4.4/4.3.4.4/4.5.4.4/ 4.3.2.2/1.0.4.3/1.2.1.1/1.0.1.1/1.2.1.1/1.0.1.1//

BAR1:4.4.4.3/2.2.1.0/1.1.1.2/1.1.1.0/1.1.1.2/1.1.1.0/ 1.1.1.2/3.3.4.5/4.4.4.3/4.4.4.5/4.4.4.3/4.4.4.5//

BAR2:1.1.1.2/3.3.4.5/4.4.4.3/4.4.4.5/4.4.4.3/4.4.4.5/ 4.4.4.3/2.2.1.0/1.1.1.2/1.1.1.0/1.1.1.2/1.1.1.0//

In such a method, yarns of the front face are essentially the ones which achieve the connection between both faces and therefore the spacer. Thus, the bar BE1 is involved in both the formation of a lap of the front face and in the formation of the spacer.

Alternatively, the knit is formed by knitting threaded yarns, one full stitch, one empty stitch, on four guide bars BAV, BE1, BAR1 and BAR2, the bars BAV and BE1 forming two laps of yarns producing the front face, the bars BAR1 and BAR2 forming two laps of yarns producing the rear face and the bar BE1 forming the spacer, said laps being knitted according to the scheme below according to the ISO 11676 standard:

BAV1:4.3.2.2/1.0.1.1/1.2.1.1/1.0.1.1/1.2.1.1/1.0.1.1/ 1.2.3.3/4.5.4.4/4.3.4.4/4.5.4.4/4.3.4.4/4.5.4.4//

BE1:1.2.3.3/4.5.2.1/4.3.4.5/4.5.4.4/4.3.4.5/4.5.4.4/ 4.3.2.2/1.0.3.4/1.2.1.0/1.0.1.1/1.2.1.0/1.0.1.1//

BAR1:4.4.4.3/2.2.1.0/1.1.1.2/1.1.1.0/1.1.1.2/1.1.1.0/ 1.1.1.2/3.3.4.5/4.4.4.3/4.4.4.5/4.4.4.3/4.4.4.5//

BAR2:1.1.1.2/3.3.4.5/4.4.4.3/4.4.4.5/4.4.4.3/4.4.4.5/ 4.4.4.3/2.2.1.0/1.1.1.2/1.1.1.0/1.1.1.2/1.1.1.0//

In such a method, the bar BE1 is still involved in both the formation of a lap of the front face and in the formation of the spacer, but its scheme has been modified so that the connecting yarns define in addition a set of parallel or oblique yarns not crossing each other and not obstructing the pores of the two opposite faces. Such an embodiment brings additional connections between the front and the rear faces: such additional connections between the front and the rear face, with connecting yarns which are yarns from a lap of the front face, bring additional resistance to compressive force to the knitted structure, as well as an optimum thickness to the three-dimensional structure of the knit.

In another embodiment of the prosthesis according to the invention, the knit is formed by knitting threaded yarns 1 full stitch, 1 empty stitch, on six guide bars BAV1, BAV2, BE1, BE2, BAR1 and BAR2, the bars BAV1 and BAV2 forming two laps of yarns forming the front face, the bars BAR1 and BAR2 forming two laps of yarns producing the rear face and the bars BE1 and BE2 forming the spacer, said laps being knitted according to the scheme below according to the ISO 11676 standard:

BAV1: 1.0.1.1/ 1.2.1.1/ 1.0.1.1/ 2.3.2.2/ 2.1.2.2/ 2.3.3.3/ 4.5.4.4/4.3.4.4/4.5.4.4/3.2.3.3/ 3.4.3.3/ 3.2.2.2//

BAV2: 4.5.4.4/ 4.3.4.4/ 4.5.4.4/ 3.2.3.3/ 3.4.3.3/ 3.2.2.2/ 1.0.1.1/1.2.1.1/1.0.1.1/2.3.2.2/2.1.2.2/2.3.3.3//

BE1: 1.1.1.0/ 1.0.1.0/ 1.0.1.1/ 1.1.1.0/ 2.3.2.3/ 2.3.2.2/ 2.2.2.3/2.3.2.3/2.3.2.2/2.2.2.3/1.0.1.0/ 1.0.1.1//

BE2: 2.2.2.3/ 2.3.2.3/ 2.3.2.2/ 2.2.2.3/ 1.0.1.0/ 1.0.1.1/ 1.1.1.0/1.0.1.0/1.0.1.1/1.1.1.0/2.3.2.3/ 2.3.2.2//

BAR1: 2.2.1.0/ 1.1.1.2/ 1.1.1.0/ 1.1.2.3/ 2.2.2.1/ 2.2.2.3/ 3.3.4.5/4.4.4.3/4.4.4.5/4.4.3.2/3.3.3.4/ 3.3.3.2//

BAR2: 3.3.4.5/ 4.4.4.3/ 4.4.4.5/ 4.4.3.2/ 3.3.3.4/ 3.3.3.2/ 2.2.1.0/1.1.1.2/1.1.1.0/1.1.2.3/2.2.2.1/ 2.2.2.3//

In such a method, the spacer is formed by means of two bars BE1 and BE2, the yarns of which are dedicated to the formation of the spacer.

In an embodiment, at least one of the faces of the knit of the prosthesis according to the invention is covered with an anti-adhesion coating, in particular in order to avoid the formation of undesired post-surgical severe fibrous adhesions.

By «anti-adhesion» in the sense of the present application, is meant a smooth and non-porous biocompatible material or coating which does not provide any space for cell recolonization and avoiding that surrounding organs adhere onto the prosthesis.

The anti-adhesion material or coating may be selected from bioresorbable materials, non-bioresorbable materials and mixtures thereof.

Non-bioresorbable anti-adhesion materials may be selected from polytetrafluoroethylene, polysiloxanes, polyurethanes, stainless steels, derivatives of precious metals and their mixtures.

Preferentially, said anti-adhesion material or coating is bioresorbable: bioresorbable materials suitable for said anti-adhesion coating may be selected from collagens, for example oxidized collagen, oxidized celluloses, polyacrylates, trimethylene carbonates, caprolactones, dioxanones, glycolic acid, lactic acid, glycolides, lactides, polysaccharides for example chitosans, polyglucuronic acids, hyaluronic acids, dextrans, fucans, polyethylene glycols, glycerol and mixtures thereof.

In an embodiment of the invention, the material forming the anti-adhesion coating is a hydrophilic bioresorbable material, preferably selected from the group formed by collagens, polysaccharides and mixtures thereof. Among the collagens which may be used according to the invention, mention may be made of:

1) collagen, the helical structure of which is at least partly thermo-denaturated, without any hydrolytic degradation, the preparation method of which is described in WO99/06080 the contents of which is incorporated to the present application by reference,
2) native, non-heated, film collagen with or without glycerin, crosslinked by gamma irradiation or by any other chemical or physical means,
3) and/or mixtures thereof.

Among the polysaccharides which may used as a resorbable hydrophilic material according to the invention, mention may be made of oxidized cellulose, hyaluronic acid, starch, chitosan, crosslinked dextrans and/or mixtures thereof. All these materials are well known to one skilled in the art. As an oxidized cellulose suitable for the present invention, mention may be made of the product sold under the trade name of «Interceed®» by Ethicon. As hyaluronic acid suitable for the present invention, mention may be made of the product sold under the trade name of «Hyalobarrier®» by Fidia Advanced Biopolymers, or of the product sold under the trade name of «Seprafilm®» by Genzyme.

During the implantation of the prosthesis according to the invention, for example as a wall reinforcement during the treatment of a hernia, the anti-adhesion coating provides protection at least during the initial healing phase to the knit of the prosthesis at the location where this adherent coating is present, i.e. the covered face(s) of the knit is(are) not exposed to inflammatory cells such as granulocytes, monocytes, macrophages or further giant multi-nucleated cells generally activated by the surgical gesture. Indeed, at least during the initial healing phase, the duration of which may vary from about 5 to 10 days, only the anti-adhesion coating is accessible by the different factors such as proteins, enzymes, cytokines or cells of the inflammatory line.

In the case when the anti-adhesion coating consists of non-resorbable materials, it thus protects the knit before and after implantation, over the whole period of implantation of the prosthesis.

Moreover, by means of the anti-adhesion coating, the surrounding fragile tissues such as hollow viscera are for example in particular protected from the formation of undesired post-surgical severe fibrous adhesions.

In the case when the anti-adhesion material comprises a bioresorbable material, it is preferable to select a bioresorbable material which is not resorbed before several days so that the anti-adhesion coating may ensure its function of protecting the surrounding organs during the days following the operation, and, until cell rehabilitation of the prosthesis protects these organs in turn.

In an embodiment, the anti-adhesion coating is in the form of a bioresorbable textile. For example, the bioresorbable textile comprises oxidized cellulose. Such a textile is for example described in US2007/0032805, the contents of which is incorporated into the present application by reference.

In an embodiment, the anti-adhesion coating is in the form of a bioresorbable film.

In an embodiment, the anti-adhesion coating is a film of a mixture of collagen and glycerol: the preparation of such a film is described in patents U.S. Pat. Nos. 6,451,032, 6,165,488 and 6,391,939, the contents of which are incorporated into the present application by reference.

In an embodiment, the anti-adhesion coating is a film of a mixture of collagen and chitosan. The preparation of such a film is for example described in document US2010/0016872, the contents of which is incorporated into the present application by reference.

In an embodiment, the anti-adhesion coating is a film of a mixture of collagen and of fucan as described in document US-2009-0005867, the contents of which is incorporated into the present application by reference. In an embodiment, the anti-adhesion coating is a film of a polysaccharide derivative as described in patent U.S. Pat. No. 6,264,702, the contents of which is incorporated into the present application by reference.

In an embodiment, the anti-adhesion coating is a film of cellulose as described in document WO2010/052585, the contents of which is incorporated into the present application by reference.

In an embodiment, the prosthesis according to the invention further comprises at least one textile layer in addition to said openworked three-dimensional knit, said textile layer being attached to one face of said knit. The textile layer may be any mesh, woven fabric, knit, non-woven fabric, made in a biocompatible material, in particular by means of biocompatible yarns, such as for example multifilament yarns, monofilament yarns and combinations thereof. Preferably, the textile is openworked. The textile may be a knit either identical or different from said openworked three-dimensional knit; it may thus be made according to the same weaves or not, with the same yarns or with different yarns.

Said textile layer may have the same shape as the shape of the openworked three-dimensional knit or a different shape. The textile layer may be attached to one face of the openworked three-dimensional knit in a continuous way or in a discrete way, by any attachment means, such as for example by sewing, by adhesive, by welding or by a combination of these means.

In an embodiment, as the openworked three-dimensional knit is in the form of a continuous part having a periphery, the textile layer has a shape with a periphery substantially identical with that of said part, said knit and said textile layer being attached to each other at their respective periphery, said textile layer being provided with a central aperture.

Preferably, when the prosthesis comprises an anti-adhesion coating as described above and a textile layer as described above, the anti-adhesion coating is present on the face of the knit opposite to the face where the textile layer is attached.

In such an embodiment, the textile layer, because of the presence of its central aperture, forms a kind of skirt which may effectively be used by the surgeon upon implanting the prosthesis, as an attachment means, by suturing this skirt to the abdominal wall.

Figure 2:
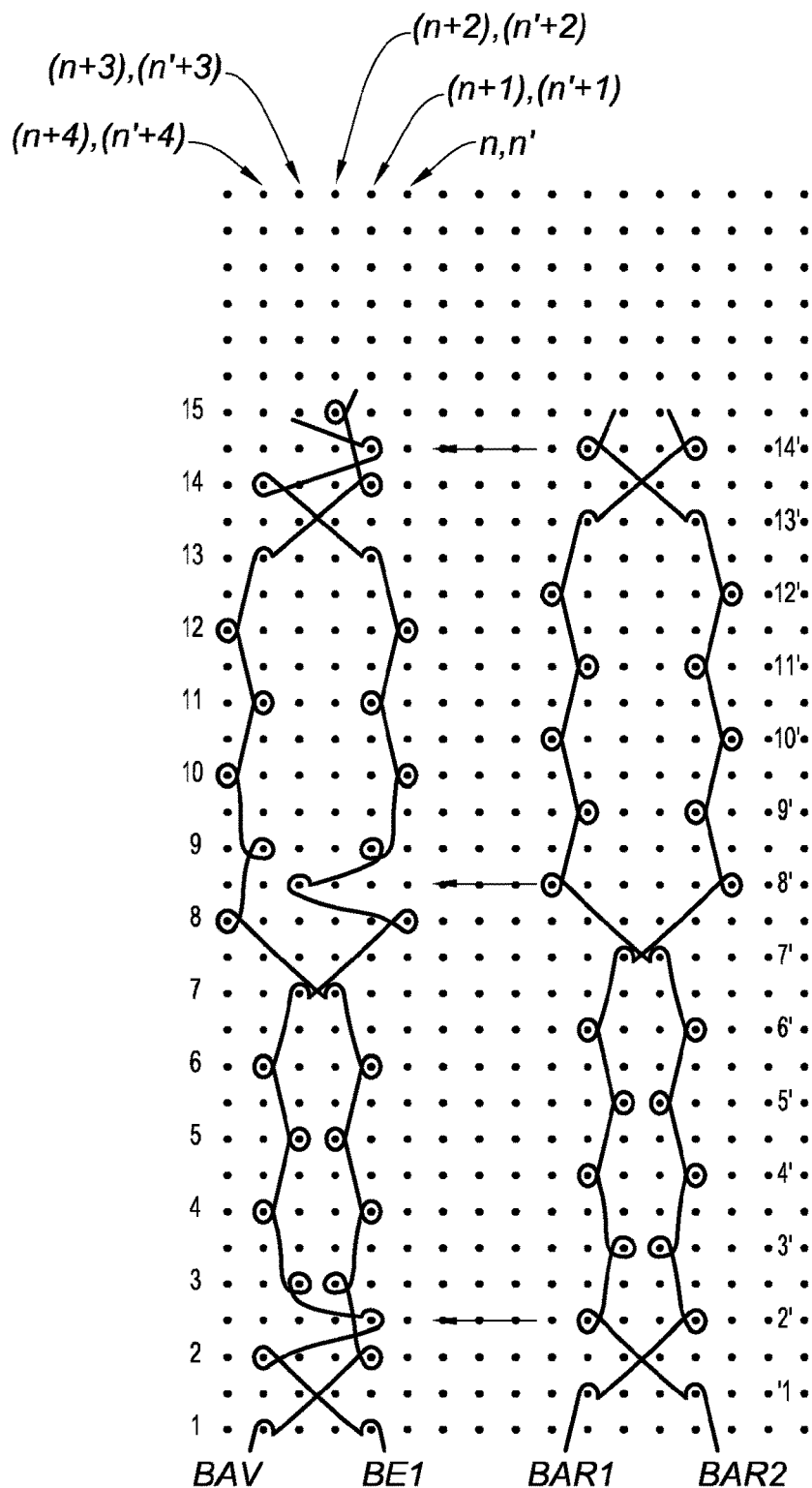
Figure 3:
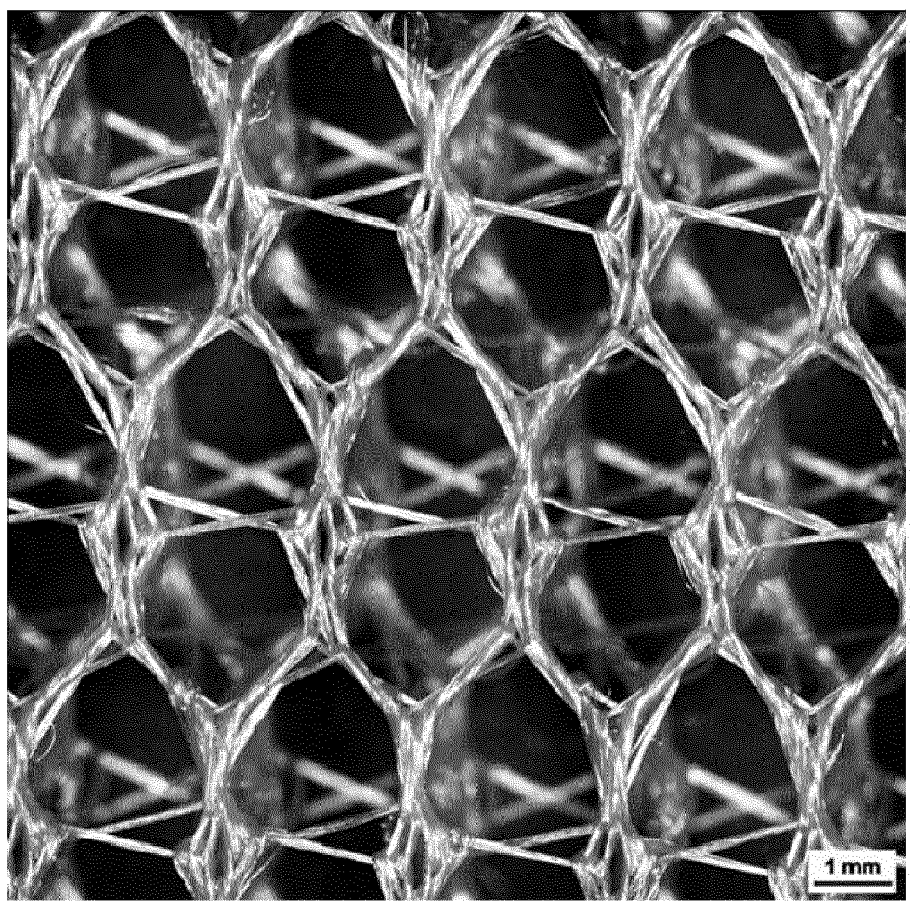
Figure 4:
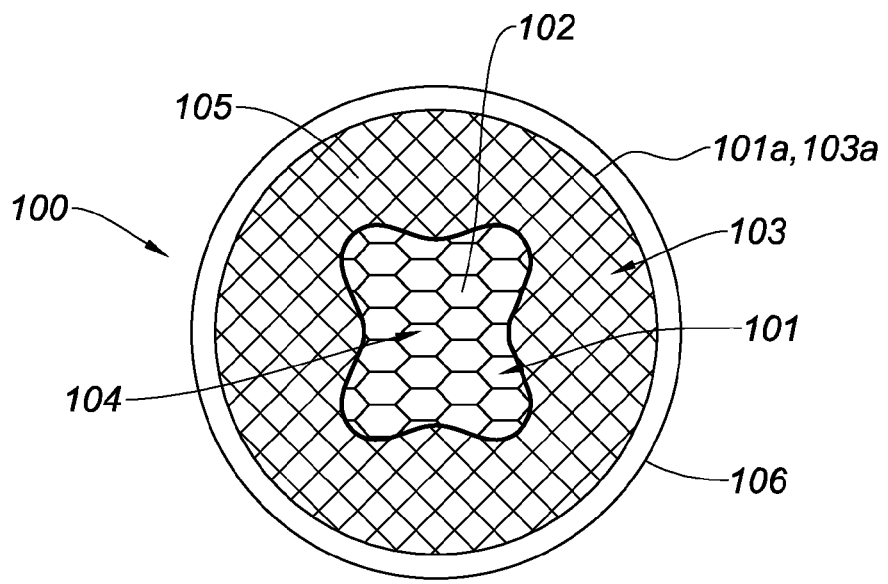
Figure 5:
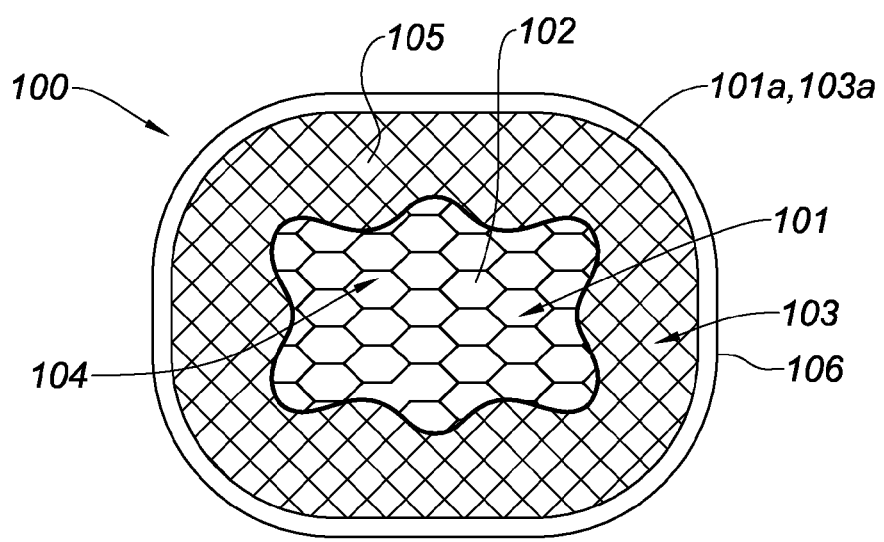
Figure 6:
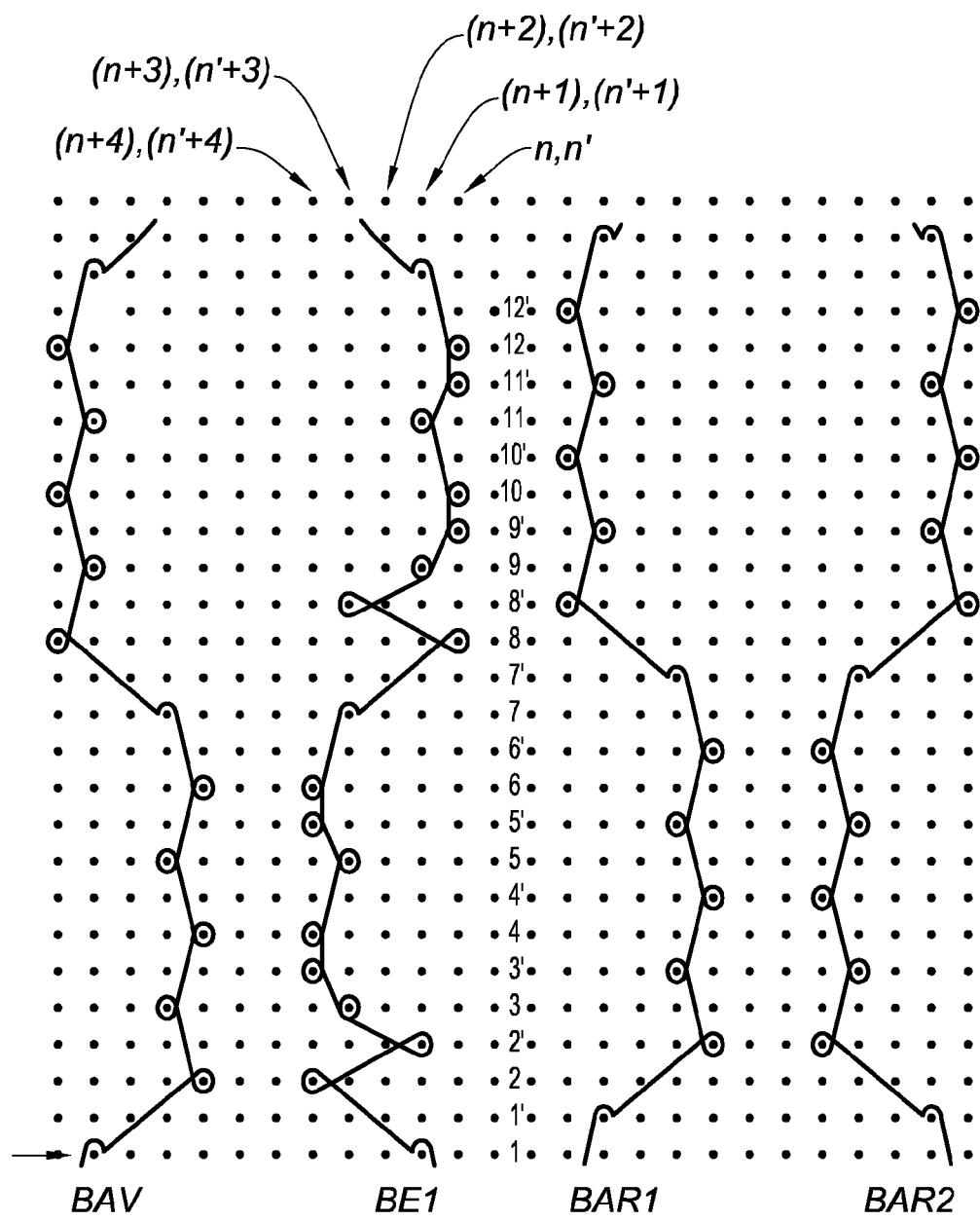
Figure 7:
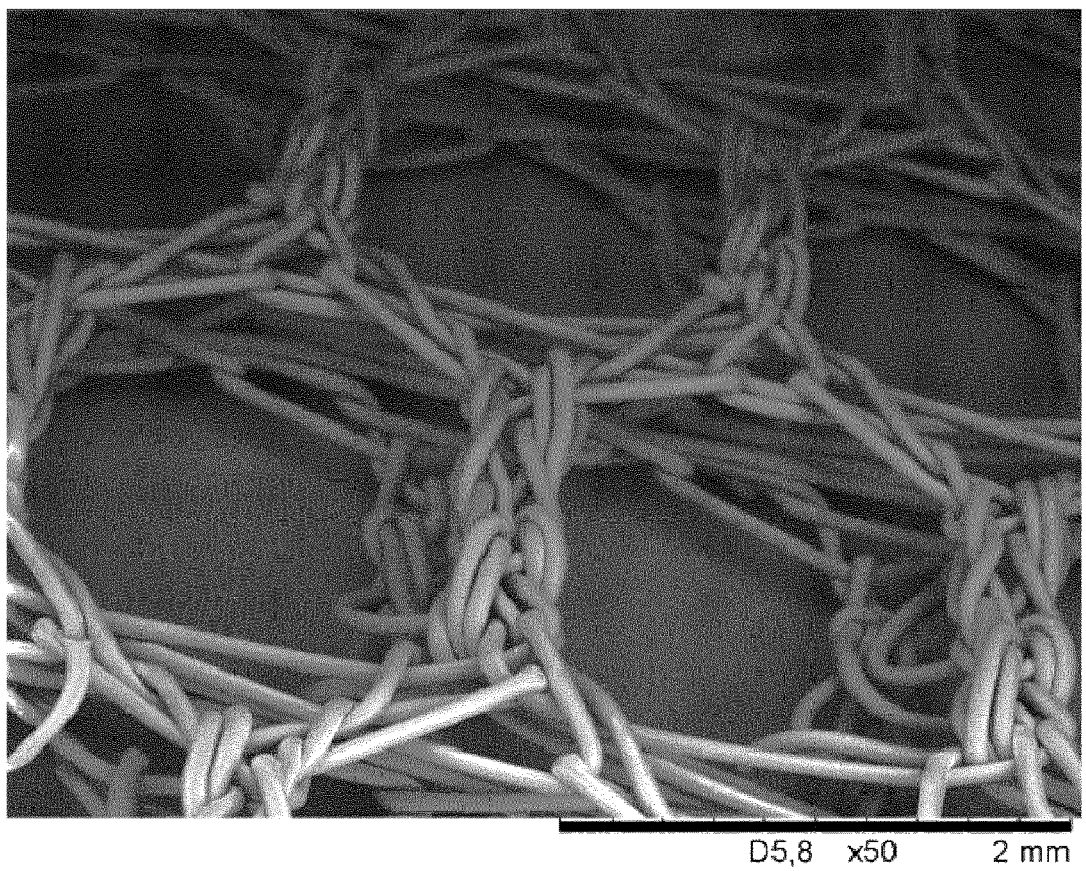

The invention will be better understood from the detailed description and the examples which follow, as well as with the figures wherein:

FIG. 1 is a view of the weave of a knit of a prosthesis according to the invention, FIG. 2 is a view of the weave of a knit of another embodiment of a prosthesis according to the invention, FIG. 3 is a scanning electron microscope view of one face of the knit obtained with the weave of FIG. 1, FIG. 4 is a top view of an embodiment of a prosthesis according to the invention, FIG. 5 is a top view of another embodiment of a prosthesis according to the invention, FIG. 6 is a view of the weave of a knit of another embodiment of a prosthesis according to the invention, FIG. 7 is a scanning electron microscope view of one face of the knit obtained with the weave of FIG. 6.

With reference to FIG. 4, a prosthesis 100 according to the invention is illustrated, comprising an openworked three-dimensional knit 101 comprising a front face 102 and a rear face (not visible in the figure): this knit 101 may be produced according to Example 1 below or according to Example 2 or according to Example 3 below. Thus, each face of the knit 101 is formed with one or more laps of yarns defining pores on said face, a face being bound to the opposite face by connecting yarns defining a spacer, the connecting yarns are distributed so that they define an entanglement of yarns which cross each other at the spacer, without obstructing the pores of the two opposite faces.

In the illustrated example, the knit 101 is in the form of a round part and has a circular periphery 101a. The prosthesis 100 further comprises a textile layer 103, having a periphery 103a substantially identical with that of the knit 101. The textile layer 103 is attached through its periphery 103a to the periphery 101a of the knit 101, and it has a central aperture 104: the textile layer 103 thereby forms a free skirt 105. During the implantation of the prosthesis 100 at a defect of the abdominal wall, for example in the treatment of a hernia, the surgeon may suture this free skirt 105 to the abdominal wall in order to effectively attach the prosthesis 100.

The prosthesis 100 further comprises an anti-adhesion coating in the form of a film 106 covering the rear face of the knit 101. In the illustrated example, the film 106 slightly juts out from the peripheries (101a, 103a) of the knit 101 and of the textile layer 103. Preferably, the film is obtained from a mixture of oxidized collagen and glycerol as described in patents U.S. Pat. Nos. 6,451,032, 6,165,488 and 6,391,939.

Such a film 106 prevents the formation of post-surgical fibrous adhesions.

By the properties of the three-dimensional knit as mentioned in Examples 1, 2 and 3 below, the prosthesis according to the invention as described in FIG. 4 has excellent three-dimensional stability and therefore a good capability for cell recolonization, even when the prosthesis is subject to pressure forces tending to press both faces against each other, as this may be accomplished by abdominal pressure. The prosthesis according to the invention also has excellent resistance to suture.

In FIG. 5, for which the references designating the same elements as for FIG. 4 have been retained, is illustrated a prosthesis 100 similar to the one of FIG. 4, but the open-worked three-dimensional knit 101 has the shape of a globally rectangular part.

The present application also describes a method for treating hernia consisting of providing a prosthesis according to the invention and of implanting it at the hernial defect: for example the face of the knit covered with the anti-adhesion coating is placed facing the abdominal cavity while the non-covered face, either provided or not with an additional textile layer forming a skirt, is placed facing the abdominal wall, with view to cell recolonization. When the prosthesis comprises a skirt as described above, the surgeon may directly attach the skirt of the prosthesis to the abdominal wall by means of sutures or clamps.

EXAMPLE 1

A knit suitable for the prosthesis according to the invention is produced with 50 decitex multi-filament polyester yarns, number of filaments per yarn:22.

The knit is produced on a two-bed Rachel knitting machine with 6 threaded guide bars 1 full stitch, 1 empty stitch, according to the following weave according to the ISO 11676 standard:

BAV1: 1.0.1.1/ 1.2.1.1/ 1.0.1.1/ 2.3.2.2/ 2.1.2.2/ 2.3.3.3/ 4.5.4.4/4.3.4.4/4.5.4.4/3.2.3.3/3.4.3.3/ 3.2.2.2//

BAV2: 4.5.4.4/ 4.3.4.4/ 4.5.4.4/ 3.2.3.3/ 3.4.3.3/ 3.2.2.2/ 1.0.1.1/1.2.1.1/1.0.1.1/2.3.2.2/2.1.2.2/2.3.3.3//

BE1: 1.1.1.0/ 1.0.1.0/ 1.0.1.1/ 1.1.1.0/ 2.3.2.3/ 2.3.2.2/ 2.2.2.3/2.3.2.3/2.3.2.2/2.2.2.3/1.0.1.0/ 1.0.1.1//

BE2: 2.2.2.3/ 2.3.2.3/ 2.3.2.2/ 2.2.2.3/ 1.0.1.0/ 1.0.1.1/ 1.1.1.0/1.0.1.0/1.0.1.1/1.1.1.0/2.3.2.3/ 2.3.2.2//

BAR1: 2.2.1.0/ 1.1.1.2/ 1.1.1.0/ 1.1.2.3/ 2.2.2.1/ 2.2.2.3/ 3.3.4.5/4.4.4.3/4.4.4.5/4.4.3.2/3.3.3.4/ 3.3.3.2//

BAR2: 3.3.4.5/ 4.4.4.3/ 4.4.4.5/ 4.4.3.2/ 3.3.3.4/ 3.3.3.2/ 2.2.1.0/1.1.1.2/1.1.1.0/1.1.2.3/2.2.2.1/ 2.2.2.3//

This weave is illustrated in FIG. 1, in which the bars BAV1, BAV2, BE1, BE2, BAR1 and BAR2, are indicated with for each bar the path of a yarn (indicated in solid lines). In this figure, the numbers 1, 2, 3, . . . 12 indicate the rows of stitches of the front face; the numbers 1', 2', 3', . . . , 12' indicate the rows of stitches of the rear face. Also in this figure, a vertical sequence of points represents two columns of stitches, both front and rear, facing each other. In FIG. 1, the columns are indicated as n, n', (n+1), (n'+1), (n+2) and (n'+2).

In the present example the yarns of the BAV1 and BAV2 bars form the front face, the yarns of the BE1 and BE2 bars form the spacer and the yarns of the BAR1 and BAR2 bars form the rear face. In the present example, the connecting yarns are therefore yarns from laps dedicated to the formation of the spacer, i.e. the laps obtained with the BE1 and BE2 bars.

The weave followed for the front face produces a front face comprising pores. Also, the weave followed for the rear face produces a face comprising pores. The pores of the front face are substantially facing the pores of the rear face.

As this appears in FIG. 1, the yarn of the BE1 bar, at the row 4' and at the column n' of the rear face, does not connect column n of the 5$^{th}$ row of the front face, but it connects column (n+2). By doing this, it connects the rear face to the front face obliquely and not perpendicularly to these faces. Next, this yarn at the row 10' of the rear face, connects column (n'+2) to column n at the 11$^{th}$ row of the front face. In the present example, x and x' as defined in the present application are therefore each equal to 2.

The yarn of the BE2 bar is also involved in the formation of the spacer, symmetrically to the yarn of the BE1 bar.

Thus, the spacer obtained is formed with connecting yarns which regularly cross each other.

The thereby obtained spacer is particularly resistant to compressive forces tending to press the front face onto the rear face. Subject to such forces, the spacer does neither collapse nor lie down thereby retaining its three-dimensional structure to the knit.

The obtained knit has the following properties:

1°) Thickness: 1.7 mm

By its structure, the knit of the present example substantially retains its height even when it is subject to a compressive force tending to press its front face onto the rear face.

2°) Transparence and size of the pores for both front and rear faces:

small pores (width×height): 2.0×2.4 mm
large pores (width×height): 2.1×2.5 mm

By the structure of the knit of the present example, the pores of the front face remain facing the pores of the rear face, even when the knit is subject to a compressive force tending to compress its front face onto its rear face.

FIG. 3 is a view taken with a scanning electron microscope of one face of the knit of the present example. As this is apparent from this view, the pores of the front face are distinctly seen (the closest to the apparatus taking the photograph) and it is also possible to distinguish in the background the pores of the rear face: the pores of the front face and those of the rear face are facing each other. Thus, the knit has excellent transparence which allows the surgeon to handle a prosthesis comprising such a knit with facility and to easily position it, in particular with respect to the surrounding organs. Indeed, the knit of the prosthesis allows the surgeon to have good visibility in transparence of the surrounding organs.

3°) Suture strength, as measured according to the NF S94-8012007 standard "Reinforcement implants set into place via a vaginal route for an urge and/or prolapsus urinary incontinence cure for pelvic organs—pre-clinical tests and clinical tests"—§ 5.2.3, 5 samples 50×100 mm, USP 2/0 suture yarn, crosshead speed: 100 mm/min in the warp direction: 30±3 N
in the weft direction: 46±2 N The above test is conducted on a tensile testing machine Hounsfield HSKS-SN 0589.

The knit retains its three-dimensional structure even when it is subject to compressive forces tending to press its front face onto its rear face.

This knit is useful for manufacturing reinforcement prosthesis for example for repairing hernias. It is sufficient to cut out the intended shape, for example a rectangular (see FIG. 5) or circular shape (see FIG. 4), in the knit of the present example in order to obtain a prosthesis which may be used as a wall reinforcement for treating hernia. A prosthesis according to the invention may consist of a knit according to the present example, alone, cut to the intended shape. Alternatively, the prosthesis may further comprise an anti-adhesion coating and/or one or more additional textile layers, as described with reference to FIGS. 4 and 5.

EXAMPLE 2

A knit suitable for the prosthesis according to the invention is produced with 88 dtex monofilament polyester yarns.

The knit is produced on a two-bed Rachel knitting machine with 4 threaded guide bars, 1 full stitch, 1 empty stitch, according to the following weave, according to the ISO 11676 standard:

BAV:4.3.2.2/1.0.1.1/1.2.1.1/1.0.1.1/1.2.1.1/1.0.1.1/ 1.2.3.3/4.5.4.4/4.3.4.4/4.5.4.4/4.3.4.4/4.5.4.4//

BE1:1.2.3.3/4.5.1.2/4.3.4.4/4.5.4.4/4.3.4.4/4.5.4.4/ 4.3.2.2/1.0.4.3/1.2.1.1/1.0.1.1/1.2.1.1/1.0.1.1//

BAR1:4.4.4.3/2.2.1.0/1.1.1.2/1.1.1.0/1.1.1.2/1.1.1.0/ 1.1.1.2/3.3.4.5/4.4.4.3/4.4.4.5/4.4.4.3/4.4.4.5//

BAR2:1.1.1.2/3.3.4.5/4.4.4.3/4.4.4.5/4.4.4.3/4.4.4.5/ 4.4.4.3/2.2.1.0/1.1.1.2/1.1.1.0/1.1.1.2/1.1.1.0

This weave is illustrated in FIG. 2, in which the bars BAV, BE1, BAR1, and BAR2, are indicated with for each bar the path of a yarn (indicated in solid line). In this figure, the numbers 1, 2, 3, . . . 15 indicate the rows of the stitches of the front face; the numbers 1', 2', 3', . . . , 14' indicate the rows of the stitches of the rear face. Also on this figure, a vertical sequence of points illustrates two columns of stitches, both front and rear, facing each other. In FIG. 2, the columns are indicated as n, n', (n+1), (n'+1), (n+2), (n'+2), (n+3), (n'+3), (n+4) and (n'+4).

In the present example, the yarns of the BAV and BE1 bars form the front face, the yarns of the BAR1 and BAR2 bars form the rear face. In the present example, the connecting yarns are therefore yarns from a lap of the front face, i.e. the lap obtained with the BE1 bar. Thus, in the present example, there are no laps of connecting yarns dedicated to the formation of the spacer.

The weave followed for the front face produces a front face comprising pores. Also, the weave followed for the rear face produces a face comprising pores. The pores of the front face are substantially facing the pores of the rear face.

As this appears in FIG. 2, the yarn forming the spacer is the yarn of the BE1 bar which, at row n° 2 and at column (n+4), connects the front face to row n° 2' of the rear face and to the column (n'+1) (see the arrow in the figure). By doing this, it rejoins the front face to the rear face obliquely and not perpendicularly to these faces: in this example, the yarn is shifted by three columns and x', as defined in the present application, is equal to 3. This yarn then connects row 2', column (n'+1) of the rear face to row 3, column (n+3) of the front face. By doing this it rejoins the rear face to the front face obliquely and not perpendicularly to these faces: in this example, the yarn is shifted by two columns and x, as defined in the present application, is equal to 2.

Next this yarn connects the $8^{th}$ row and column n of the front face to row 8', column (n'+3) of the rear face (see the arrow in the figure). By doing this, it rejoins the front face to the rear face obliquely and not perpendicularly to these faces and x is equal to 3. Next, the yarn connects row 8', column (n'+3) of the rear face to row 9, column (n+1) of the front face and here, x' is equal to 2.

Thus, the obtained spacer is formed with connecting yarns which regularly cross each other thereby generating an optimum entanglement of yarns not parallel with each other.

The thereby obtained spacer is particularly resistant to compressive forces tending to press the front face onto the rear face. Subject to such forces, the spacer neither collapses nor lies down parallel to the front and rear faces, thereby retaining its three-dimensional knitted structure.

This knit is useful for manufacturing reinforcement prosthesis for example for repairing hernias. It is sufficient to cut out the intended shape, for example a rectangular (see FIG. 4) or circular shape (see FIG. 5), in the knit of the present example in order to obtain a prosthesis which may be used as a wall reinforcement for treating a hernia. A prosthesis according to the invention may consist of a knit according to the present example, alone, cut out to the intended shape. Alternatively, the prosthesis may further comprise an anti-adhesion coating and/or one or more additional textile layers, as described with reference to FIGS. 4 and 5.

EXAMPLE 3

A knit suitable for the prosthesis according to the invention is produced with 88 dtex monofilament polyester yarns.

The knit is produced on a two-bed Rachel knitting machine with 4 threaded guide bars, 1 full stitch, 1 empty stitch, according to the following weave, according to the ISO 11676 standard:

BAV:4.3.2.2/1.0.1.1/1.2.1.1/10.1.1/1.2.1.1/1.0.1.1/ 1.2.3.3/4.5.4.4/4.3.4.4/4.5.4.4/4.3.4.4/4.5.4.4//

BE1:1.2.3.3/4.5.2.1/4.3.4.5/4.5.4.4/4.3.4.5/4.5.4.4/ 4.3.2.2/1.0.3.4/1.2.1.0/1.0.1.1/1.2.1.0/1.0.1.1//

BAR1:4.4.4.3/2.2.1.0/1.1.1.2/1.1.1.0/1.1.1.2/1.1.1.0/ 1.1.1.2/3.3.4.5/4.4.4.3/4.4.4.5/4.4.4.3/4.4.4.5//

BAR2:1.1.1.2/3.3.4.5/4.4.4.3/4.4.4.5/4.4.4.3/4.4.4.5/ 4.4.4.3/2.2.1.0/1.1.1.2/1.1.1.0/1.1.1.2/1.1.1.0

This weave is illustrated in FIG. 6, in which the bars BAV, BE1, BAR1, and BAR2, are indicated with for each bar the path of a yarn (indicated in solid line). In this figure, the numbers 1, 2, 3, . . . 15 indicate the rows of the stitches of the front face; the numbers 1', 2', 3', . . . , 14' indicate the rows of the stitches of the rear face. Also on this figure, a vertical sequence of points illustrates two columns of stitches, both front and rear, facing each other. In FIG. 6, the columns are indicated as n, n', (n+1), (n'+1), (n+2), (n'+2), (n+3), (n'+3), (n+4) and (n'+4).

In the present example, the yarns of the BAV and BE1 bars form the front face, the yarns of the BAR1 and BAR2 bars form the rear face. In the present example, the connecting yarns are therefore yarns from a lap of the front face, i.e. the lap obtained with the BE1 bar. Thus, in the present example, there are no laps of connecting yarns dedicated to the formation of the spacer.

The weave followed for the front face produces a front face comprising pores. Also, the weave followed for the rear face produces a face comprising pores. The pores of the front face are substantially facing the pores of the rear face.

As this appears in FIG. 6, the yarn forming the spacer is the yarn of the BE1 bar which, at row n° 2 and at column (n+4), connects the front face to row n° 2' of the rear face and to the column (n'+1). By doing this, it rejoins the front face to the rear face obliquely and not perpendicularly to these faces: in this example, the yarn is shifted by three columns and x', as defined in the present application, is equal to 3. This yarn then connects row 2', column (n'+1) of the rear face to row 3, column (n+3) of the front face. By doing this it rejoins the rear face to the front face obliquely and not perpendicularly to these faces: in this example, the yarn is shifted by two columns and x, as defined in the present application, is equal to 2.

This yarn also connects the $8^{th}$ row and column n of the front face to row 8', column (n'+3) of the rear face. By doing this, it rejoins the front face to the rear face obliquely and not perpendicularly to these faces and x is equal to 3. Next, the yarn connects row 8', column (n'+3) of the rear face to row 9, column (n+1) of the front face and here, x' is equal to 2.

Thus, the obtained spacer comprises connecting yarns which regularly cross each other thereby generating an optimum entanglement of yarns not parallel with each other.

In addition, in the present example, the yarn of the BE1 bar forms additional connections between the front face and the rear face, in which the connecting yarns do not cross each other: these additional connections may be seen on FIG. 6 at rows 3, 5, 9 and 11.

Indeed, at row n° 3 and at column (n+3), the yarn connects the front face to row n° 3' of the rear face and to the column (n'+4). By doing this, it rejoins the front face to the rear face obliquely and not perpendicularly to these faces: in this example, the yarn is shifted by one column. This yarn then connects row 3', column (n'+4) of the rear face to row 4, column (n+4) of the front face. By doing this it rejoins the rear face to the front face perpendicularly to these faces, with no shift of column. The same phenomenon is repeated starting at row 5.

In addition, at row n° 9 and at column (n+1), the yarn connects the front face to row n° 9' of the rear face and to the column n'. By doing this, it rejoins the front face to the rear face obliquely and not perpendicularly to these faces: in this example, the yarn is shifted by one column. This yarn then connects row 9', column n' of the rear face to row 10, column n of the front face. By doing this it rejoins the rear face to the front face perpendicularly to these faces, with no shift of column. The same phenomenon is repeated starting at row 11.

Such additional connections between the front and the rear face, with connecting yarns which are yarns from a lap of the front face, bring additional resistance to compressive force to the knitted structure.

The thereby obtained spacer is particularly resistant to compressive forces tending to press the front face onto the rear face. Subject to such forces, the spacer neither collapses nor lies down parallel to the front and rear faces, thereby retaining its three-dimensional knitted structure.

The obtained knit has the following properties:

1°) Thickness: 1.3 mm

By its structure, the knit of the present example substantially retains its height even when it is subject to a compressive force tending to press its front face onto the rear face.)

2°) Transparence and size of the pores for both front and rear faces:

pores (width×height): 2.0×3.3 mm

By the structure of the knit of the present example, the pores of the front face remain facing the pores of the rear face, even when the knit is subject to a compressive force tending to compress its front face onto its rear face.

FIG. 7 is a view taken with a scanning electron microscope of one face of the knit of the present example. As this is apparent from this view, the pores of the front face and of the rear face are aligned on each other so that it is possible to clearly see the background behind the knit through the knit: the pores of the front face and those of the rear face are facing each other. Thus, the knit has excellent transparence which allows the surgeon to handle a prosthesis comprising such a knit with facility and to easily position it, in particular with respect to the surrounding organs. Indeed, the knit of the prosthesis allows the surgeon to have good visibility in transparence of the surrounding organs.)

3°) Suture strength, as measured according to the NF S94-8012007 standard "Reinforcement implants set into place via a vaginal route for an urge and/or prolapsus urinary incontinence cure for pelvic organs—pre-clinical tests and clinical tests"—§ 5.2.3, 5 samples 50×100 mm, USP 2/0 suture yarn, crosshead speed: 100 mm/min in the warp direction: 46±3 N
in the weft direction: 50±6 N The above test is conducted on a tensile testing machine Hounsfield H5KS-SN 0589.

The knit retains its three-dimensional structure even when it is subject to compressive forces tending to press its front face onto its rear face.

This knit is useful for manufacturing reinforcement prosthesis for example for repairing hernias. It is sufficient to cut out the intended shape, for example a rectangular (see FIG. 4) or circular shape (see FIG. 5), in the knit of the present example in order to obtain a prosthesis which may be used as a wall reinforcement for treating a hernia. A prosthesis according to the invention may consist of a knit according to the present example, alone, cut out to the intended shape. Alternatively, the prosthesis may further comprise an anti-adhesion coating and/or one or more additional textile layers, as described with reference to FIGS. 4 and 5.

The invention claimed is:

1. A method of forming a three-dimensional prosthetic knit comprising knitting threaded yarns on at least four guide bars BAV, BE1, BAR1 and BAR2, the guide bars BAV and BE1 forming two laps of yarns producing a front face of the knit, the guide bars BAR1 and BAR2 forming two laps of yarns producing a rear face of the knit and the guide bar BE1 forming connecting yarns defining a spacer connecting the front face to the rear face of the knit, said laps being knitted according to a scheme below in accordance with the ISO 11676 standard:

BAV:4.3.2.2/1.0.1.1/1.2.1.1/1.0.1.1/1.2.1.1/1.0.1.1/
1.2.3.3/4.5.4.4/4.3.4.4/4.5.4.4/4.3.4.4/4.5.4.4//
BAR1:4.4.4.3/2.2.1.0/1.1.1.2/1.1.1.0/1.1.1.2/1.1.1.0/
1.1.1.2/3.3.4.5/4.4.4.3/4.4.4.5/4.4.4.3/4.4.4.5//
BAR2:1.1.1.2/3.3.4.5/4.4.4.3/4.4.4.5/4.4.4.3/4.4.4.5/
4.4.4.3/2.2.1.0/1.1.1.2/1.1.1.0/1.1.1.2/1.1.1.0//.

2. The method of claim 1, wherein the knitting of guide bar BE1 is according to a scheme below in accordance with the ISO 11676 standard:

BE1:1.2.3.3/4.5.1.2/4.3.4.4/4.5.4.4/4.3.4.4/4.5.4.4/
4.3.2.2/1.0.4.3/1.2.1.1/1.0.1.1/1.2.1.1/1.0.1.1//.

3. The method of claim 1, wherein the knitting of guide bar BE1 is according to a scheme below in accordance with the ISO 11676 standard:

BE1:1.2.3.3/4.5.2.1/4.3.4.5/4.5.4.4/4.3.4.5/4.5.4.4/
4.3.2.2/1.0.3.4/1.2.1.0/1.0.1.1/1.2.1.0/1.0.1.1//.

4. The method of claim 1, wherein the threaded yarns are one full stitch, one empty stitch.

5. The method of claim 1, wherein no laps of the connecting yarns are dedicated to the formation of the spacer.

6. The method of claim 1, wherein the knit further comprises pores of the front face and pores of the rear face, wherein the pores of the front face substantially face the pores of the rear face.

7. The method of claim 1, wherein the connecting yarns regularly cross each other thereby generating an optimum entanglement of yarns not parallel with each other, not crossing each other and not obstructing the pores of the two opposite faces.

8. The method of claim 1, further comprising attaching a textile layer to one face of the knit.

9. The method of claim 8, wherein the textile layer comprises a central aperture.

10. The method of claim 1, further comprising covering at least one face of the knit with an anti-adhesion coating.

11. The method of claim 10, wherein the anti-adhesion coating is in the form of a bioresorbable textile.

12. The method of claim 10, wherein the anti-adhesion coating is in the form of a bioresorbable film.

13. The method of claim 8, further comprising covering a face of the knit, opposite the face including the textile layer attached thereto, with an anti-adhesion coating.

14. A method of forming a three-dimensional prosthetic knit comprising knitting threaded yarns on at least six guide bars BAV1, BAV2, BE1, BE2, BAR1 and BAR2, the guide bars BAV1 and BAV2 forming two laps of yarns producing a front face of the knit, the guide bars BAR1 and BAR2 forming two laps of yarns producing a rear face of the knit and the guide bars BE1 and BE12 forming connecting yarns defining a spacer connecting the front face to the rear face of the knit, said laps being knitted according to a scheme below in accordance with the ISO 11676 standard:

BAV1:1.0.1.1/1.2.1.1/1.0.1.1/2.3.2.2/2.1.2.2/2.3.3.3/
4.5.4.4/4.3.4.4/4.5.4.4/3.2.3.3/3.4.3.3/3.2.2.2//
BAV2:4.5.4.4/4.3.4.4/4.5.4.4/3.2.3.3/3.4.3.3/3.2.2.2/
1.0.1.1/1.2.1.1/1.0.1.1/2.3.2.2/2.1.2.2/2.3.3.3//
BE1:1.1.1.0/1.0.1.0/1.0.1.1/1.1.1.0/2.3.2.3/2.3.2.2/
2.2.2.3/2.3.2.3/2.3.2.2/2.2.2.3/1.0.1.0/1.0.1.1//
BE2:2.2.2.3/2.3.2.3/2.3.2.2/2.2.2.3/1.0.1.0/1.0.1.1/
1.1.1.0/1.0.1.0/1.0.1.1/1.1.1.0/2.3.2.3/2.3.2.2//
BAR1:2.2.1.0/1.1.1.2/1.1.1.0/1.1.2.3/2.2.2.1/2.2.2.3/
3.3.4.5/4.4.4.3/4.4.4.5/4.4.3.2/3.3.3.4/3.3.3.2//
BAR2:3.3.4.5/4.4.4.3/4.4.4.5/4.4.3.2/3.3.3.4/3.3.3.2/
2.2.1.0/1.1.1.2/1.1.1.0/1.1.2.3/2.2.2.1/2.2.2.3//.

15. The method of claim 14, wherein the threaded yarns are one full stitch, one empty stitch.

16. The method of claim 14, wherein the laps of the connecting yarns are dedicated to the formation of the spacer.

17. The method of claim 14, wherein the knit further comprises pores of the front face and pores of the rear face, wherein the pores of the front face substantially face the pores of the rear face.

18. The method of claim 14, wherein the connecting yarns regularly cross each other thereby generating an optimum entanglement of yarns not parallel with each other, not crossing each other and not obstructing the pores of the two opposite face.

19. The method of claim 14, further comprising attaching a textile layer to one face of the knit.

20. The method of claim 19, wherein the textile layer comprises a central aperture.

21. The method of claim 14, further comprising covering at least one face of the knit with an anti-adhesion coating.

22. The method of claim 21, wherein the anti-adhesion coating is in the form of a bioresorbable textile.

23. The method of claim 21, wherein the anti-adhesion coating is in the form of a bioresorbable film.

24. The method of claim 19, further comprising covering a face of the knit, opposite the face including the textile layer attached thereto, with an anti-adhesion coating.

\* \* \* \* \*